United States Patent
Kim et al.

(10) Patent No.: US 10,201,485 B2
(45) Date of Patent: Feb. 12, 2019

(54) WASHING COMPOSITION

(71) Applicant: AMOREPACIFIC CORPORATION, Seoul (KR)

(72) Inventors: Hyun Na Kim, Yongin-si (KR); Byung Ha Kang, Yongin-si (KR); Dae-Kyeong Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 44 days.

(21) Appl. No.: 15/495,259

(22) Filed: Apr. 24, 2017

(65) Prior Publication Data
US 2017/0224599 A1    Aug. 10, 2017

Related U.S. Application Data

(63) Continuation-in-part of application No. PCT/KR2015/002881, filed on Mar. 24, 2015.

(30) Foreign Application Priority Data

Oct. 30, 2014  (KR) .................. 10-2014-0149421

(51) Int. Cl.
*C11D 1/00* (2006.01)
*C11D 1/38* (2006.01)
(Continued)

(52) U.S. Cl.
CPC .............. *A61K 8/416* (2013.01); *A61K 8/022* (2013.01); *A61K 8/0254* (2013.01); *A61K 8/046* (2013.01); *A61K 8/24* (2013.01); *A61K 8/26* (2013.01); *A61Q 5/02* (2013.01); *A61Q 19/10* (2013.01); *C11D 3/1253* (2013.01);
(Continued)

(58) Field of Classification Search
CPC ........... C11D 1/00; C11D 1/38; C11D 3/1246; C11D 3/1226; C11D 3/128; C11D 7/14; A61Q 5/02; A61Q 19/00; A61K 8/24; A61K 8/25; A61K 8/26; A61K 8/41
See application file for complete search history.

(56) References Cited

U.S. PATENT DOCUMENTS 6,245,343 B1    6/2001  Roulier et al.
2003/0134761 A1  7/2003  Sebillotte-Arnaud et al.
(Continued)

FOREIGN PATENT DOCUMENTS

EP    0919611 A1    2/1999
EP    2105469 A1    9/2009
(Continued)

OTHER PUBLICATIONS

International Search Report dated Jun. 30, 2015 for PCT/KR2015/002881 and English translation.
(Continued)

*Primary Examiner* — Brian P Mruk
(74) *Attorney, Agent, or Firm* — Lucas & Mercanti, LLP (57) ABSTRACT

The present invention relates to a washing composition comprising a powder of which surface is hydrophobic, and more specifically, relates to a washing composition comprising a powder in which an alkyl group of a surfactant attached to the surface thereof is oriented towards an outermost shell, thereby the surface of the powder being hydrophobically modified.

11 Claims, 6 Drawing Sheets

(51) Int. Cl.

| | | |
|---|---|---|
| *C11D 7/14* | (2006.01) | |
| *A61Q 5/02* | (2006.01) | |
| *A61Q 19/00* | (2006.01) | |
| *A61K 8/24* | (2006.01) | |
| *A61K 8/25* | (2006.01) | |
| *A61K 8/26* | (2006.01) | |
| *A61K 8/41* | (2006.01) | |
| *A61Q 19/10* | (2006.01) | |
| *A61K 8/02* | (2006.01) | |
| *A61K 8/04* | (2006.01) | |
| *C11D 3/12* | (2006.01) | |

(52) U.S. Cl.
 CPC .... *A61K 2800/31* (2013.01); *A61K 2800/412* (2013.01); *A61K 2800/612* (2013.01)

(56) References Cited

U.S. PATENT DOCUMENTS

| | | |
|---|---|---|
| 2009/0252691 A1 | 10/2009 | Gartstein et al. |
| 2012/0177712 A1* | 7/2012 | Bhattacharya ......... A01N 25/26 424/401 |
| 2013/0029932 A1 | 1/2013 | Kachi et al. |

FOREIGN PATENT DOCUMENTS

| | | | |
|---|---|---|---|
| JP | H11512472 A | 10/1999 | |
| JP | 2003113073 A | 4/2003 | |
| JP | 2012167035 A | 9/2012 | |
| KR | 19990045091 A | 6/1999 | |
| KR | 20000006050 A | 1/2000 | |
| KR | 1020050067234 A | 6/2005 | |
| KR | 20110059985 A | 6/2011 | |
| KR | 20110102415 A | 9/2011 | |
| KR | 20130028062 A | 3/2013 | |
| KR | 1020130037898 A | 4/2013 | |
| WO | 97/10321 A1 | 3/1997 | |
| WO | 2004024119 A1 | 3/2004 | |
| WO | 20090009796 A1 | 1/2009 | |
| WO | 2014102032 A1 | 7/2014 | |
| WO | WO 2014/102032 * | 7/2014 | ............... A61K 8/26 |

OTHER PUBLICATIONS

Stablization of Foams with Inorganic Colloidal Particles, Langmuir, vol. 22, No. 26, Dec. 1, 2006, pp. 10983-10988, Urs T. Gonzenbach et al.

European Search Report, 15855961.7-1468 / 3214161 PCT/KR2015/ 15002881, dated Oct. 10, 2017.

* cited by examiner

WASHING COMPOSITION

CROSS-REFERENCE TO RELATED APPLICATIONS

This application is a continuation-in-part of PCT/KR2015/002881, filed Mar. 24, 2015, which claims the benefit of Korean Patent Application No. 10-2014-0149421, filed Oct. 30, 2014, the contents of each of which are incorporated herein by reference.

FIELD OF THE INVENTION

The present invention relates to a washing composition comprising a powder of which surface is hydrophobic. More specifically, the present invention relates to a washing composition improved in foaming ability, which comprises a powder in which an alkyl group of a surfactant attached to the surface thereof is oriented towards an outermost shell, thereby the surface of the powder being hydrophobically modified.

BACKGROUND ART

The biggest purpose of a hair cleanser is to maintain the cleanliness of scalp and hair by removing a waste, for example, sebum and to control the condition of scalp. The waste adsorbed on the scalp is acidified to proliferate bacteria, thereby causing unpleasant smell and itch. In order to remove the waste, a hair cleanser of which main ingredient is an anionic surfactant is generally used. The anionic surfactant is penetrated between the waste and the hair on the scalp, whereby the adsorptive power of waste is weakened and may be easily washed.

The surfactant which is the main ingredient of hair cleanser is generally anionic. The anionic surfactant plays a role as a primary surfactant and imparts a shampoo with such basic functions as detergency and foaming ability. The secondary surfactant is a co-surfactant and used for the purpose of improving durability and stability of bubbles and maintaining viscosity.

However, the anionic surfactant may cause irritation to the scalp. Also, the continuous and repeated washing by the anionic surfactant may interfere the normal metabolism of the scalp to cause various scalp disorders. Eco-friendly sugars and amino acid compounds have been developed to complement these problems. The amino acids occurring naturally in large quantities are studied in various fields according to the well-being trend in these days as a new alternative resource. Also, the raw material industry has continued effort to develop a surfactant that gives less irritation to the skin as possible or is skin-friendly.

On the other hand, as the ingredient of a hair cleanser, the case of using a powder is extremely rare. Only, the Korean Patent Laid-open Publication No. 10-2011-0102415 discloses a hair detergent composition containing a sebum-absorbent, and describes the possibility of use of a powder as a sebum-absorbent. However, this is used for the effects of sebum-adsorption from the hair, removal of dead skin cell, etc., which are resulted from the oil-absorption capacity of the powder itself. Also, the effect of improving the foaming ability depending on the particle size or surface characteristics of a certain powder has been neither realized in a product nor found in any prior literature.

Typical detergents contain the anionic surfactant in the amount of about 14-20% by weight for detergency and foaming ability. However, the anionic surfactant is one of the skin irritants, and thus it tends to increase the skin irritation when it remains on, or is exposed to, the skin for a prolonged period of time. Accordingly, recently, there are attempts to reduce the amount of anionic surfactant, but the reduction of foaming ability becomes the greatest limitation in such attempts.

SUMMARY OF THE INVENTION

The present invention has been made in order to solve the above problems and provides a washing composition comprising an anionic surfactant in the low amount of 13% by weight or less, but also comprising a powder of which surface is hydrophobically modified for reinforcing the foaming ability declined due to the reduced amount of the anionic surfactant. The powder of which surface is hydrophobically modified has the particle size of 0.1 to 10 μm and is contained in the amount of 0.1 to 5% by weight based on the total weight of the washing composition. The powder contained in the washing composition of the present invention has the form that a surfactant for modifying the surface is attached to the hydrophilic moiety hydroxy group (—OH) of the powder. It shows the feature of hydrophobicity since the alkyl group (C5-C24) of the surfactant for modifying the surface is oriented towards an outermost shell. At this time, it is additionally possible to enhance the efficiency of surface modification by replacing the hydrophilic moiety hydroxy group (—OH) of the powder with phosphate group (—PO$_4$), pyrophosphate group (—P$_2$O$_7$), or phosphite group (—OPO$_2$H$_2$) to widen the surface area. The composition may also additionally contain a co-surfactant to compensate for the low content of anionic surfactant.

If the presently invented washing composition which comprises a powder of which surface is hydrophobically modified is applied, it is possible to prepare a detergent having excellent detergency and foaming ability while minimizing skin irritation by lowering the content of anionic surfactant.

DETAILED DESCRIPTION OF THE INVENTION

The present invention relates to a washing composition comprising a powder of which surface is hydrophobically modified. In the washing composition, the relatively hydrophobic air (gas phase) is emulsified in water (liquid phase) by the surfactant contained in the composition to produce a foam, wherein the foam, an emulsified particle, can be stabilized when the powder is stably arranged on the interfacial film.

The above effect comes from the effect of pickering stabilization of the powder. The pickering technique means a technique which stabilizes two different phases using a powder, and is well known as a concept of pickering emulsion. In the same way as the concept of pickering emulsion, the powder arrangement on the interfacial (liquid/gas) film may be expected to be different depending on the surface charge properties and the particle size of the powder.

Hereinafter, the main compositions that can be included in the washing composition of the present invention and their characteristics are explained.

(1) Powder of which Surface is Hydrophobically Modified

The washing composition of the present invention comprises a powder of which surface is hydrophobically modified for the purpose of reinforcing the foaming ability and the foam retaining ability declined due to the reduced amount of anionic surfactant.

Figure 1:
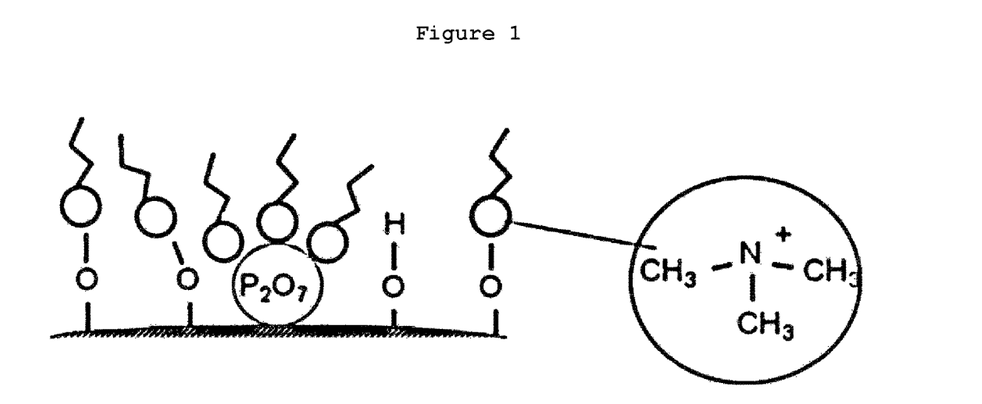
FIG. 1 is a diagram illustrating the principle of surface modification of the powder used in the washing composition of the present invention.

In the present invention, the powder has the form that a surfactant for modifying the surface is attached to the hydrophilic moiety hydroxy group (—OH) on the surface of the powder as depicted in FIG. 1. It is characterized by having a hydrophobic surface since an alkyl group of the surfactant attached as above is oriented towards an outermost shell. At this time, it is possible to enhance the efficiency of surface modification by replacing the hydrophilic moiety hydroxy group (—OH) of the powder with phosphate group (—PO$_4$), pyrophosphate group (—P$_2$O$_7$), or phosphite group (—OPO$_2$H$_2$) to widen the surface area. It may be also possible to impart hydrophobicity to the surface by orienting the alkyl group at the end of the surfactant for modifying the surface towards an outermost shell.

The powder capable of being used in the present invention may be selected from, for example, kaolin, silica, talc, mica, and alumina, and preferably is kaolin.

Kaolin is generally called China clay or porcelain clay, which is obtained from decomposition of feldspar by weathering and is widely distributed on earth's crust. Its composition may be largely different depending on the ore deposit. However, according to the degree of weathering of feldspar and the geological history, kaolin comprises silica, mica, and other clay minerals, in particular unweathered feldspar, as the secondary mineral component besides the main minerals kaolinite and halloysite. All the kaolin minerals have the chemical formula Al$_2$Si$_2$O$_5$(OH)$_4$ (kaolinite) or Al$_2$O$_3$·2SiO$_2$·2H$_2$O (halloysite), but their crystal structures are different from each other. The inorganic materials, silica, alumina, magnesium, organic composite materials, germanium, far-infrared radiation, etc. extracted from kaolin are known to advantageously act to the human body thereby providing remarkable effect to the skin care. It also has the effects of odor adsorption, deodorization, etc. and thus widely utilized as a raw material for cosmetics such as powder, mask pack, etc. Furthermore, since it is a white soft powder, absorbs moisture and oil, and has good covering ability, it is suitably used as a cleanser for absorbing the sweat and oil secreted from the skin.

The powder of which surface is hydrophobically modified has the particle size of most preferably 0.1 to 10 μm. The particle size of less than 0.1 μm has little effect in the foam stabilization and that of exceeding 10 μm may cause the powder to be remained in the scalp and hair to negatively affect the skin feeling.

The powder of which surface is hydrophobically modified is preferably contained in the amount of 0.1 to 5% by weight based on the total weight of the washing composition. The content of less than 0.1% by weight results the insufficient foam stabilization effect of the powder, whereby enhancement of foaming ability and foam retaining ability may not be expected. And the content of exceeding 5% by weight may deteriorate the skin feeling due to the unique stiffness of powder when it is used.

The surfactant for modifying the surface of powder becomes hydrophobic by the alkyl group, which appropriately has the carbon number of C5 to C24, and preferably it reacts with the hydrophilic group of the powder. It may be one or more selected from the group consisting of cetrimonium chloride (CTAC), cetrimonium bromide, steartrimonium chloride and behentrimonium chloride. More preferably, cetrimonium chloride (CTAC) having the following formula 1 is used:

<Formula 1>

(2) Anionic Surfactant

The washing composition of the present invention has the purpose of reducing the amount of anionic surfactant used to alleviate the irritation to the scalp or hair. Thus, the anionic surfactant may be contained in the amount of 13% by weight or less, preferably 3 to 13% by weight based on the total weight of the washing composition. The content of less than 3% by weight may deteriorate detergency and that of exceeding 13% by weight may irritate the skin.

The anionic surfactant has excellent detergency, penetration force, dispersibility, and emulsifying capacity, and it is ionized in water so that its hydrophilic moiety becomes negative (−) ion. Typically, it includes the three types of acids, i.e., carboxylic acid (—COOH), sulfuric acid ester (—OSO$_3$H), and sulfonic acid (—SO$_3$H), most of which are used as a soluble salt.

As the applicable anionic surfactant, those known in the art may be used. For example, alkyl sulfates, ethoxylated alkyl sulfates, alkyl ethoxy carboxylates, alkyl glyceryl ether sulfonates, ethoxy ether sulfonates, methyl acyl taurates, alkyl sulfosuccinates, alkyl ethoxy sulfosuccinates, alpha-sulfonated fatty acids, alkyl phosphate esters, ethoxylated alkyl phosphate esters, straight-chain alkyl benzene sulfonates, paraffin sulfonates, alpha-olefin sulfonates, alkyl alkoxy sulfates, and mixtures thereof, particularly preferably sodium laureth sulfate may be used, but not limited thereto.

(3) Non-Ionic Surfactant

The washing composition of the present invention may additionally comprise a non-ionic surfactant for the purpose of reinforcing the detergency on the scalp or hair deteriorated due to the reduced amount of anionic surfactant and at the same time minimizing the total content of surfactant. It is possible to be contained in the amount of 8% by weight or less, preferably 1 to 8% by weight based on the total weight of the washing composition. If the non-ionic surfactant is contained in the amount of less than 1% by weight, the effect of reinforcing detergency may be trivial. On the contrary, if the content exceeds 8% by weight, it may irritate the scalp. The non-ionic surfactant has the hydrophilic moiety formed through the hydrogen bond between hydroxy group (—OH) or ethylene oxide group (—OCH$_2$CH$_2$) and water instead of the hydrophilic moiety formed by ionization. It is a surfactant used in the area of emulsifier, antistatic agent, or penetrating agent. It is usually in the liquid phase and dissolved in water to be neutral. Such a non-ionic surfactant has the strong power of emulsifying water and oil and thus generally used as an emulsifier for a cream such as a treatment. It is relatively stable to the skin and thus used in most cosmetics.

As the applicable non-ionic surfactant, those known in the art may be used. For example, one or more selected from the group consisting of alcohol ethoxylates, amide ethoxylates, amine oxides, alkyl glucosides, and mixtures thereof, preferably cocamide methyl MEA, may be used.

(4) Cationic Surfactant/Amphoteric Surfactant

The washing composition of the present invention applies the non-ionic surfactant for assisting the function of anionic surfactant. However, other combinations (for example, with a cationic surfactant or with an amphoteric surfactant) are also possible. As the cationic surfactant, a quarternary ammonium and a tertiary amidoamine may be used alone or as a mixture. For example, it is possible to use the quarternary ammoniums such as behenyl trimethyl ammonium chloride, cetyl trimethyl ammonium chloride, stearyl trimethyl ammonium chloride, distearyl dimethyl ammonium chloride, etc.; and the tertiary aminoamines such as cocamido propyl dimethyl amine, stearamido propyl dimethyl amine, behenamido propyl dimethyl amine, oleamido propyl dimethyl amine, isostearamido propyl dimethyl amine, etc. Also, as the amphoteric surfactant, it is possible to use alkyl betaines, amide betaines, sulfobetaines, hydroxysulfobetaines, amidosulfobetaines, phosphobetaines, imidazolinium betaines, aminopropionic acids, amino acids, and mixtures thereof.

It is desirable to contain the cationic and/or amphoteric surfactant in the amount range of reinforcing the detergency at the level of no irritation to the skin, but which is not limited in the present invention.

BEST MODE FOR CARRYING OUT THE INVENTION

Below, the present invention will be explained more in detail by the examples. These examples are only for specifically illustrating the present invention, and it is apparent for a person of ordinary skill in the art to which the present invention pertains that the scope of the present invention is not restricted by these examples. Unless defined otherwise, the technical and scientific terms used herein have the meanings commonly understood by a person of ordinary skill in the art to which the present invention pertains. Also, repeated description for the same technical constitution and action as the prior art will be omitted.

Considering the skin feeling (feeling of residual powder on the hair, feel of powder particle, etc.) and the stability of formulation, the experiments in the following examples were carried out by making a difference on the surface charge property, provided that the average particle size was limited to the level of 10 nm to 50 μm.

Preparation Examples 1 to 4 are hair cleansers individually comprising four (4) types of commercially available powders which differ in particle size and surface property (hydrophobic/hydrophilic) from each other. Examples 1 to 4 correspond to Preparation Examples 1 to 4, respectively, whose foaming ability, foam retaining ability, antifoaming ability and hair softness during rinsing were evaluated through predetermined tests.

Preparation Examples

Table 1 summarizes the physical properties of four types of powders (Powder 1~4) which were applied to the present invention. Table 2 represents the ingredients and contents thereof (% by weight) in the hair cleansers of Preparation Examples 1 to 4 to which each powder was applied.

TABLE 1

| | Powder 1 | Powder 2 | Powder 3 | Powder 4 |
|---|---|---|---|---|
| Name | Aerosil R202 | Aerosil 200 | Hydro dry (K) | Colloidal Kaolin-BC Grade 2457 |
| Manufacturer | Evonik industries | Evonik industries | Sunjin Beauty Science Co., Ltd. | Brenntag specialties |
| INCI | Silica/Dimethicone | Colloidal Silicone Dioxide | Kaolin & Cetrimonium Chloride & Tetrasodium pyrophosphate | Kaolin $(SiO_2, AlO_2)$ |
| Particle Size | 14 nm | 12 nm | 1~7 μm | 10~20 μm |
| Surface Property | Hydrophobic | Hydrophilic | Hydrophobic | Hydrophilic |

TABLE 2

| Ingredient | Pre. Ex. 1 | Pre. Ex. 2 | Pre. Ex. 3 | Pre. Ex. 4 |
|---|---|---|---|---|
| D.I. Water | 83.92 | 83.92 | 83.92 | 83.92 |
| Aerosil R202 | 0.40 | — | — | — |
| Aerosil 200 | — | 0.40 | — | — |
| Hydro dry (K) | — | — | 0.40 | — |
| Colloidal Kaolin-BC Grade 2457 | — | — | — | 0.40 |
| Guar Hydroxypropyltrimonium Chloride | 0.20 | 0.20 | 0.20 | 0.20 |
| Disodium EDTA | 0.05 | 0.05 | 0.05 | 0.05 |
| Sodium Laureth (2EO) sulfate (SLES) | 8.50 | 8.50 | 8.50 | 8.50 |
| Cocamide Methyl MEA | 5.50 | 5.50 | 5.50 | 5.50 |
| Fragrance | 1.00 | 1.00 | 1.00 | 1.00 |
| Phenoxyethanol | 0.20 | 0.20 | 0.20 | 0.20 |
| Methylchloroisothiazolinone, Methylisothiazolinone | 0.03 | 0.03 | 0.03 | 0.03 |
| Sodium Chloride | 0.20 | 0.20 | 0.20 | 0.20 |
| Total | 100.00 | 100.00 | 100.00 | 100.00 |

Preparation Example 1 shown in Table 2 used Aerosil R202 (Trade name, Manufacturer: Evonik Industries) as the powder. Referring to Table 1, this is silica which is hydrophobically modified by arranging dimethicone on its surface and has the average particle size of about 14 nm.

Also, Preparation Example 2 used Aerosil 200 (Trade name, Manufacturer: Evonik Industries) as the powder. Referring to Table 1, this is silica of which surface is hydrophilic and has the average particle size of about 12 nm.

Preparation Example 3 used Hydro dry (K) (Trade name, Manufacturer: Sunjin Beauty Science Co., Ltd.) as the powder. Referring to Table 1, this is kaolin of which surface is hydrophobically modified by the surfactant cetrimonium chloride, and has the average particle size of about 1~7 μm. During the surface modification process, tetrasodium pyrophosphate $(Na_4P_2O_7)$ was used for maximizing the effect of surface modification by widening the surface area of hydrophilic moiety of the kaolin powder particle.

Also, Preparation Example 4 used Colloidal Kaolin-BC Grade 2457 (Trade name, Manufacturer: Brenntag Specialties) as the powder. Referring to Table 1, this is kaolin of which surface is hydrophilic and has the average particle size of about 10-20 μm.

In Table 2 above, the cationic polymer Guar Hydroxypropyltrimonium Chloride was Guarquat L80KC (Trade name, Manufacturer: KCI), the anionic surfactant Sodium Laureth Sulfate (Sodium Laureth (2E0) Sulfate; SLES) was Micolin ES270 (Trade name, Manufacturer: Miwon Chemicals), and the non-ionic surfactant Cocamide Methyl MEA was Micopol CMM (Trade name, Manufacturer: Miwon Chemicals), but they are not limited thereto. In addition, the chelating agent was disodium EDTA, the preservative was Phenoxyethanol, Methylchloroisothiazolinone and Methylisothiazolinone, and the thickener was Sodium Chloride, and some fragrance was added. But, these are optional ingredients, and there is no limit in the additional use of any optional ingredient.

In Preparation Examples 1 to 4 of Table 2, the amount of anionic surfactant was fixed to 8.5% by weight based on the total amount of washing composition to obtain a washing composition having a low content of anionic surfactant, thereby minimizing the irritation to the scalp and hair. The non-ionic surfactant was subsidiarily used in the amount of 5.5% by weight to secure the detergency.

Experiment 1

Figure 2:
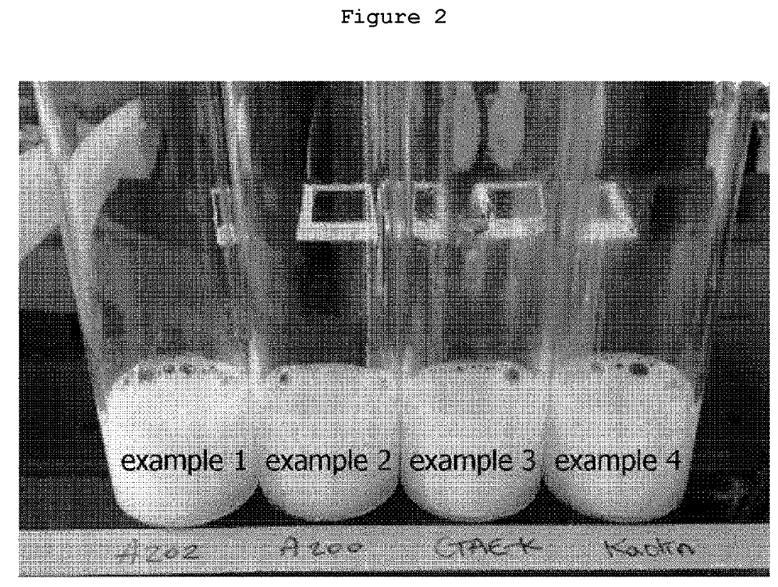
FIG. 2 compares the washing compositions of Examples 1 to 4 of the present invention before shaking.
Figure 3:
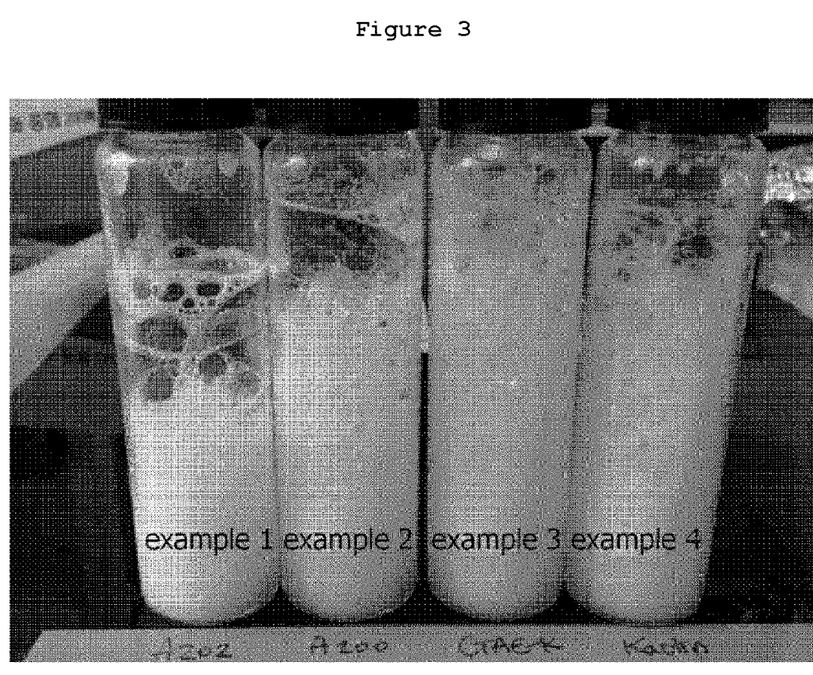
FIG. 3 compares the washing compositions of Examples 1 to 4 of the present invention right after the shaking.
Figure 4:
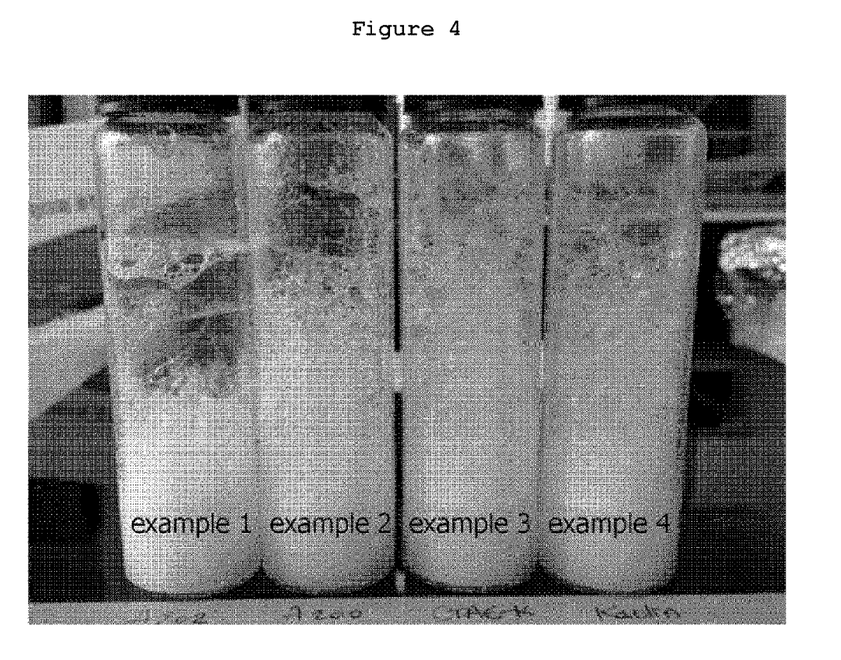
FIG. 4 compares the washing compositions of Examples 1 to 4 of the present invention after standing for 10 minutes from the shaking.

The foaming ability and the foam retaining ability of the Preparation Examples 1-4 were tested, and the results were shown in Table 3 and FIGS. 2-4. In the table and figures, the Preparation Examples 1-4 were referred to Examples 1-4, respectively.

The foaming ability was tested herein as follows: Each of the washing compositions of Preparation Examples 1 to 4 was diluted to the concentration of 5% in 100 mL of aqueous solution at 25° C. 1 g of artificial sebum was added thereto and mixed for 1 minute under 300 rpm of magnetic stirrer during which the foam generation was minimized. 10 mL thereof was introduced to a 60 mL glass vial having a diameter of 30 mm and shaken 20 times in a shaking incubator rotating 180 degrees per second. The foaming ability was defined as the height (mm) of the foam which was formed right after the shaking.

The foam retaining ability was defined herein as the height (mm) of the foam after standing for 10 minutes from the shaking.

Also, the antifoaming ability was defined herein by Equation 1 below:

$$\text{Antifoaming ability(mm)} = \text{Foaming ability(mm)} - \text{foam retaining ability(mm)} \quad \text{Equation 1}$$

FIGS. 2, 3 and 4 compare and depict the foam height of the Preparation Examples 1-4 before the shaking, right after the shaking, and after standing for 10 minutes from the shaking, respectively. The foam height in FIGS. 2 to 4 was obtained by measuring the vertical height from the bottom of the glass vial to the highest level of the foam produced inside the vial.

As can be seen from Table 3 and FIG. 3, the foaming ability, i.e., the foam height right after the shaking, was the highest in the composition of Example 3 wherein the foam reached around the bottleneck of vial. The next highest foaming ability was observed in the composition of Example 4 and the composition of Example 2 in the order, and it was confirmed that the composition of Example 1 showed the lowest foaming ability, wherein the foam reached only around the middle level of the vial. Also, as can be seen from Table 3 and FIG. 4, the foam retaining ability, i.e., the level of foam retaining, after standing for 10 minutes was considerably high in Examples 3 and 4 which showed similar level of foam height to the height right after the shaking. On the contrary, Examples 1 and 2 were confirmed to show a poor foam retaining ability since they had considerably reduced foam in comparison to that of right after the shaking.

The foaming ability and the foam retaining ability of Examples 1 to 4 as measured above, and the antifoaming ability calculated therefrom are represented in Table 3 below.

Experiment 2

Also, the hair softness during rinsing was arithmetically calculated by selecting ten (10) professional panels, letting them use the hair cleanser prepared in Examples 1 to 4, and then performing sensory evaluation on the hair softness during rinsing under the basis of from the minimum score 1 to the maximum score 9.

Results

Table 3 below summarizes the test results regarding the four (4) items of foaming ability, foam retaining ability, antifoaming ability and hair softness during rinsing of the hair cleansers of Examples 1 to 4, respectively.

TABLE 3

| Evaluation Item | Ex. 1 | Ex. 2 | Ex. 3 | Ex. 4 |
|---|---|---|---|---|
| Foaming Ability (mm) | 48 | 72 | 95 | 78 |
| Foam Retaining Ability (mm) | 33 | 62 | 91 | 75 |
| Antifoaming Ability (mm) | 15 | 10 | 4 | 3 |
| Hair Softness during Rinsing | 4 | 4 | 6 | 3 |

As shown in Table 3, the composition of Example 3 showed the foaming ability and the foam retaining ability of 95 mm and 91 mm, respectively, which were higher than any of Examples 1, 2 and 4. Accordingly, it was evaluated to have low antifoaming ability of 4 mm. Also, Example 3 showed the best hair softness during rinsing of 6. Thus, it was confirmed from the above four (4) tests that Example 3 containing Hydro dry (K) manufactured by Sunjin Beauty Science Co., Ltd. was the most appropriate as a hair cleanser in terms of foaming ability, foam retaining ability, antifoaming ability and hair softness during rinsing.

In other words, the washing composition of Example 3 which comprises kaolin having the average particle size of about 1-7 μm, of which surface is hydrophobically modified, as the powder was evaluated to be the most desirable.

Among the powders of Table 1, the hydrophilic kaolin not modified (Example 4) and the hydrophobic kaolin wherein the alkyl group is oriented on the surface by the surface modification (Example 3) cause different foaming ability and foam retaining ability, as can be seen from the results of Examples 3 and 4 of Table 3, although they have a similar particle size. Based on this result, it is assumed that the hydrophobicity produced by the alkyl group helps stabilization of foam. On the contrary, in case that a silicone group such as dimethicone is arranged on the surface of the powder to impart hydrophobicity thereto (Example 1), the antifoaming effect is rather observed. Consequently, the best foam-stabilizing effect is found in the powder wherein the surface is hydrophobically modified, in particular, the alkyl group is oriented on the surface. It is most preferable to use the powder having the particle size of about 0.1~10 μm considering the skin feeling or stability.

Experiment 3

Table 4 below compares the composition of Example 3 which shows the best results in the tests as described above and that of Comparative Example 1 which does not contain a powder.

TABLE 4

| Ingredient | Ex. 3 | Com. Ex. 1 |
|---|---|---|
| D.I. Water | 83.92 | 84.32 |
| Hydro dry (K) | 0.40 | — |
| Guar Hydroxypropyltrimonium Chloride | 0.20 | 0.20 |
| Disodium EDTA | 0.05 | 0.05 |
| Sodium Laureth (2EO) sulfate (SLES) | 8.50 | 8.50 |
| Cocamide Methyl MEA | 5.50 | 5.50 |
| Fragrance | 1.00 | 1.00 |
| Phenoxyethanol | 0.20 | 0.20 |
| Methylchloroisothiazolinone, Methylisothiazolinone | 0.03 | 0.03 |
| Sodium Chloride | 0.20 | 0.20 |
| Total | 100.00 | 100.00 |

Figure 5:
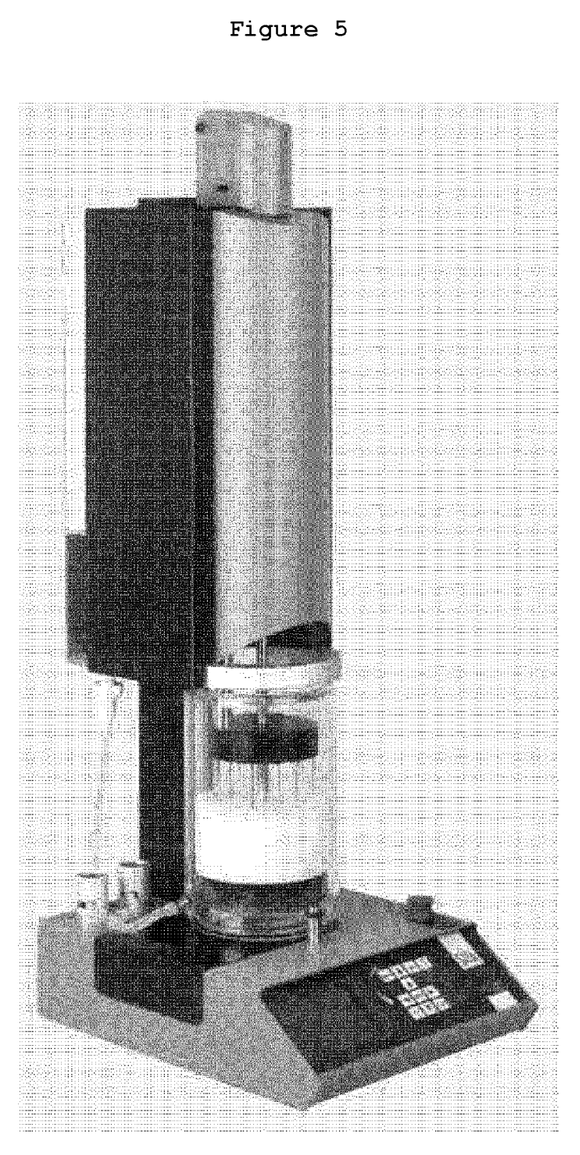
FIG. 5 is an image of the foam tester (SITA foam tester R-2000, Manufacturer: SITA Messtechnik GmbH) used for measuring the foam volumes of Example 3 of the present invention and Comparative Example 1.

First, each of the washing compositions prepared according to Example 3 and Comparative Example 1 of Table 4 was diluted in 250 mL of aqueous solution at 25° C. to obtain the concentration of 5%. Then, stirring for 20 seconds at 800 rpm in a foam tester as depicted in FIG. 5 (SITA Foam Tester R-2000, Manufacturer: SITA Messtechnik GmbH) was carried out as one set in the process of total five (5) sets, and the foam volume thus produced was measured for each set.

Figure 6:
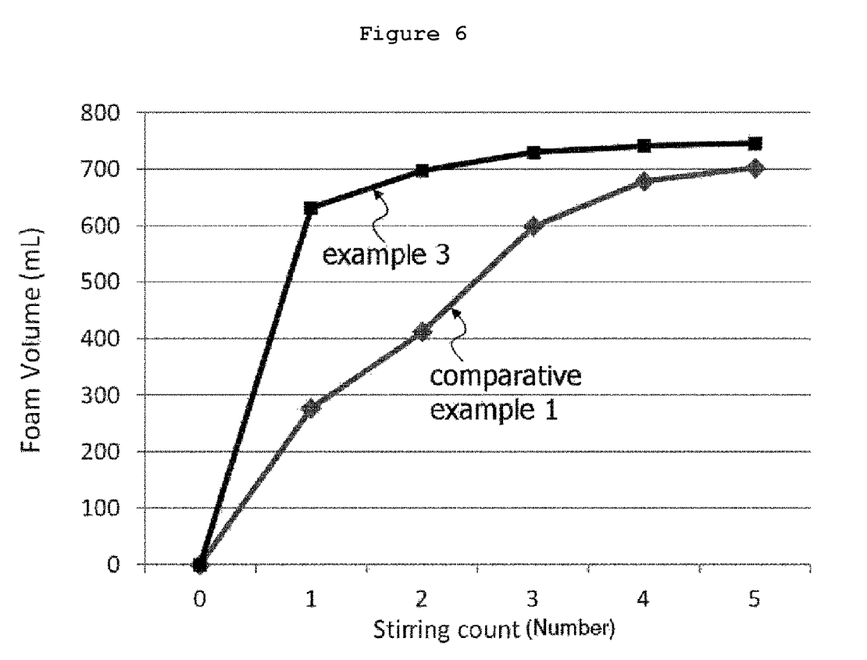
FIG. 6 is a graph showing the data of foam volumes of Example 3 of the present invention and Comparative Example 1 depending on stirring count.

FIG. 6 is a graph depicting the data of foam volumes of Example 3 of the present invention and Comparative Example 1 depending on stirring count (set). The foaming speed and foam stability of the cleanser may be confirmed by the slope of FIG. 6.

According to the graph data of FIG. 6, the foam volume initially produced was about 620 mL in Example 3 and about 280 mL in Comparative Example 1, which means that Example 3 showed about 2.2 times higher volume than Comparative Example 1. The initial slope was also higher in Example 3 than in Comparative Example 1. Thus, the foaming speed was more excellent in Example 3 than in Comparative Example 1, and it could be seen that the foam initially produced in Example 3 was retained stably even though the stirring count (set) was increased with the time lapse. In other words, it was shown that the kaolin powder of the present invention of which surface was hydrophobically modified affected not only the initial foaming ability but also the foam stability of the cleanser.

In Experiment 1, Example 3 showed the most excellent foaming ability of 95 mm. Also, in the test for measuring the foam retaining ability which is the foam height after standing for 10 minutes, Example 3 showed the highest value of 91 mm. Thus, the antifoaming ability which is a difference between the foaming ability and the foam retaining ability was 4 mm in Example 3. It may be determined that the richer foam is developed and maintained as the foaming ability and the foam retaining ability are higher and the antifoaming ability is lower. Furthermore, in the sensory evaluation on the hair softness during rinsing, Example 3 showed the most excellent result of 6. On the other hand, in a separate experiment of sensory evaluation by professional panels, a washing composition may be determined as desirable when it shows the foaming ability of 85 mm or more, the foam retaining ability of 80 mm or more, the antifoaming ability of 6 mm or less and the hair softness during rinsing of 5 or more.

In the test for Example 3 and Comparative Example 1 which does not contain a powder, Example 3 showed the foam volume of about 620 mL and Comparative Example 1 showed that of about 280 mL after the first set of stirring, which means that the initial foaming speed is more excellent in Example 3. Example 3 also maintained the initially formed foam volume even after the fifth set of stirring, which means the excellent foam stability. Such an effect comes from the hydrophobically modified kaolin powder. Thus, it can be seen that the kaolin powder affects the foaming speed and the foam stability.

The washing composition of the present invention can be applied most preferably to the hair cleanser among the external skin cleansers, but not limited thereto. It may be suitably applied to the cleansers requiring low irritation and high stability, such as for example, body wash, cleanser for pets, face wash, etc.

What is claimed is:

1. A washing composition comprising a powder with a hydrophobically modified surface,
   wherein the powder has a form that a surfactant is attached to the surface thereof, and an alkyl group of the attached surfactant is oriented towards an outermost shell, thereby the surface of the powder being hydrophobically modified, and
   wherein a hydroxy group of the powder is replaced with a phosphate group, a pyrophosphate group, or a phosphite group.

2. The washing composition of claim 1, wherein the powder has a particle size of 0.1 to 10 μm.

3. The washing composition of claim 1, wherein the powder is kaolin.

4. The washing composition of claim 1, wherein the surfactant attached to the surface of the powder is one or more selected from the group consisting of cetrimonium chloride (CTAC), cetrimonium bromide, steartrimonium chloride and behentrimonium chloride.

5. The washing composition of claim 1, wherein the powder is contained in the amount of 0.1 to 5% by weight based on the total weight of the washing composition.

6. The washing composition of claim 1, comprising an anionic surfactant in the amount of 13% by weight or less based on the total weight of the washing composition.

7. The washing composition of claim 6, further comprising a non-ionic surfactant in the amount of 8% by weight or less based on the total weight of the washing composition.

8. The washing composition of claim 1, having a foaming ability of 85 mm or more, provided that the foaming ability is defined as a foam height in mm, which is formed right after diluting a washing composition to the concentration of 5% in 100 mL of aqueous solution at 25° C., adding 1 g of artificial sebum thereto and mixing for 1 minute while minimizing the foam generation under 300 rpm of magnetic stirrer, introducing 10 mL thereof to a 60 mL glass vial having a diameter of 30 mm, and shaking 20 times in a shaking incubator rotating 180 degrees per second.

9. The washing composition of claim 8, wherein a foam retaining ability is 80 mm or more, provided that the foam retaining ability is a foam height after standing for 10 minutes from the shaking of 20 times.

10. The washing composition of claim 9, wherein an antifoaming ability is 6 mm or less, provided that Antifoaming ability (mm)=Foaming ability (mm)−Foam retaining ability (mm).

11. The washing composition of claim 1, wherein a foam volume is 500 mL or more right after diluting the washing composition in 250 mL of aqueous solution at 25° C. to obtain a concentration.

\* \* \* \* \*